United States Patent [19]
Kirby et al.

[11] Patent Number: 5,837,686
[45] Date of Patent: Nov. 17, 1998

[54] PEPTIDES AND ANTIBODIES FOR TREATMENT OF RHEUMATOID ARTHRITIS

[75] Inventors: Julian Kirby; Ian V. Lewin, both of Staffordshire; Sarita Maman, West Midlands; Denis R. Stanworth, Birmingham, all of United Kingdom

[73] Assignee: Peptide Therapeutics Limited, Cambridgeshire, England

[21] Appl. No.: 244,496

[22] PCT Filed: Nov. 25, 1992

[86] PCT No.: PCT/GB92/02174

§ 371 Date: Jul. 28, 1994

§ 102(e) Date: Jul. 28, 1994

[87] PCT Pub. No.: WO93/11153

PCT Pub. Date: Jun. 10, 1993

Related U.S. Application Data

[63] Continuation-in-part of Ser. No. 70,117, Jun. 1, 1993, abandoned.

[30] Foreign Application Priority Data

Nov. 25, 1991 [GB] United Kingdom ................ 9125024

[51] Int. Cl.⁶ .............................. A61K 38/03; C07K 4/00
[52] U.S. Cl. .............................. 514/17; 514/16; 514/18; 530/329; 530/330; 530/331
[58] Field of Search .................... 530/326, 327, 530/328, 329, 330, 331; 514/16, 17, 18

[56] References Cited

U.S. PATENT DOCUMENTS 4,692,511  9/1987  Hahn ........................................ 530/325

FOREIGN PATENT DOCUMENTS

| 0 025 897 | 4/1981 | European Pat. Off. . |
| 235391 | 9/1987 | European Pat. Off. . |
| WO 85/02625 | 6/1985 | WIPO . |
| WO 88/00240 | 1/1988 | WIPO . |
| WO 90/10228 | 9/1990 | WIPO . |
| 90/12806 | 11/1990 | WIPO . |
| WO 90/13573 | 11/1990 | WIPO . |

OTHER PUBLICATIONS

Ohta et al. "Amino acids and Peptides . . . " Chem. Pharm. Bul. vol. 31 (1983), pp. 3094–3103.

L. Adorini et al. "Interaction of an immunodominant . . . " Proc. Natl. Acad. Sci. USA, vol. 85 (Jul. 1988), pp. 5181–5185.

S.E. Funk & H. Sage. "The $Ca^{2+}$–binding glycoprotein SPARC . . . " Proc. Natl. Acad. Sci. USA, vol. 88 (Apr. 1991), pp. 2648–2652.

T.B. Tomasi, Jr. et al. "Binding of α–1 . . . " Chemical Abstracts #103073c, vol. 81, 1974, p. 340.

H. Ohtani et al. "Protein contents and binding modes . . . " Chemical Abstracts #215728m, vol. 96, 1982, p. 556.

D.R. Stanworth et al. "Immunodiagnostic assay for rheumatoid . . . " Biochem Methods #124390k, vol. 116, 1992, p. 124391.

J.W. Prahl et al. "Carboxy–terminal structure . . . " Biochemistry, vol. 10 No. 10, 1971, pp. 1808–1812.

C.B. Glaser et al. "Studies on disulfide region . . . " Chemical Abstracts #87806a, vol. 97, 1982, p. 364.

E. Mendez, et al. "Characterization of a disulfide . . . " Immunochemistry, #94083f, vol. 80, 1974, p. 94089.

B.S. Shorbrosh et al. "Molecular cloning of a putative . . . " Proc. Natl. Acad. Sci., USA, vol. 88 (Dec. 1991), pp. 10941–10945.

*Primary Examiner*—Cecilia J. Tsang
*Assistant Examiner*—Anish Gupta
*Attorney, Agent, or Firm*—Nixon & Vanderhye

[57] ABSTRACT

A synthetic peptide of not more than 20 amino acid residues or analogue thereof comprising a thiol-active cysteine residue and at least two positively charged amino acid residues situated on (but not necessarily adjacent to) the N-terminal side, on (but not necessarily adjacent to) the C-terminal side or on (but not necessarily adjacent to) both the N- and C-terminal sides of the thiol-active cysteine for use in therapy.

12 Claims, 2 Drawing Sheets

PEPTIDES AND ANTIBODIES FOR TREATMENT OF RHEUMATOID ARTHRITIS

This Appln is a 371 of PCT/US94/06128 Jun. 1, 1994 which is a CIP of Ser. No. 08/070,117 Jun. 1, 1993 (abandoned).

FIELD OF THE INVENTION

This invention is in the field of rheumatoid arthritis (RA) treatment.

DESCRIPTION OF THE PRIOR ART

Rheumatoid arthritis, (RA), has been described as an unresolved systemic inflammation in which immune dysfunction and genetic susceptibility play roles. There is increasing evidence that the major immunopathological factor in RA is the covalently linked complex between serum IgA and $\alpha_1$-antitrypsin ($\alpha_1$AT), a major anti-protease. This disulphide-bridged complex is found to be present at abnormally high levels in the sera and joint fluids of RA patients. In vitro studies have revealed that the complex is capable of inducing the release of tissue-degradative enzymes from mouse macrophages, whilst injection of the complex itself into the knee joints of rabbits or mice causes the onset of RA like arthritis.

It has been shown that a fall in the circulating level of the complex is observed in those rheumatoid patients who respond favourably to treatment with so-called "second-line" anti-rheumatic drugs such as D-penicillamine (dimethyl cysteine) and myocrisin (sodium aurothiomalate). This can be explained by these thiol compounds forming mixed disulphides with the thiol-active IgA produced in large amounts by rheumatoid patients, thereby preventing its reaction with $\alpha_1$-antitrypsin to form the undesired IgA-$\alpha_1$AT complex (Stanworth, D. R.—Immunology Today 1985, 6, 43).

There is a problem with the currently available thiol-based anti-rheumatic drugs such as D-penicillamine in that they are relatively toxic, causing many rheumatoid patients to end their treatment prematurely.

It is therefore desirable to find alternative means of combatting rheumatoid arthritis.

SUMMARY OF THE INVENTION

RA patients are known to produce grossly elevated levels of thiol-reactive IgA which is thought to be covalently bonded to $\alpha_1$AT to form the IgA-$\alpha_1$AT complex. It has now been found that certain peptides, fulfilling certain specified requirements as to their charged amino acid groups and capable of interacting with thiol-reactive IgA at a thiol-reactive cysteine residue, are capable of dissociating IgA-$\alpha_1$AT complex or preventing IgA-$\alpha_1$AT complex formation. Dissociation of complex or prevention of complex formation might be expected to have a favourable effect against clinical RA and is therefore of therapeutic potential. Monoclonal antibodies raised against IgA-$\alpha_1$AT complex are also capable of alleviating the effects of IgA-$\alpha_1$AT complex in RA patients.

Accordingly, the invention provides a synthetic peptide of not more than 20 amino acid residues or an analogue thereof wherein the analogue is at least partly non-peptide in nature comprising a thiol-active cysteine residue and at least two positively charged amino acid residues situated on (but not necessarily adjacent to) the N-terminal side, or on (but not necessarily adjacent to) the C-terminal side or on (but not necessarily adjacent to) both the N- and C-terminal sides of the thiol-active cysteine residue for use in therapy. The term "comprising" here and throughout the text, means "consisting of or including" and likewise for other parts of the verb. Thus the total peptide can extend beyond the peptide defined above, having additional peptide sequences or non-peptide sequences at one or both ends of the peptide. The peptide will normally have from 3 to 20 amino acid residues, more typically from 4 to 10 amino acid residues. Terminal functions of the peptide can be blocked, e.g. by N-acylation or C-amidation, or the peptides can be derivatised in any conventional manner.

The invention also provides a ligand comprising an antibody domain specific for an antigenic determinant of a complex of human IgA and $\alpha_1$-antitrypsin, said antibody domain being substantially non-reactive with free human IgA and free human $\alpha_1$-antitrypsin, for use in therapy.

This definition covers monoclonal and polyclonal antibodies, antigen binding fragments thereof, e.g. Fab' and F(ab')$_2$ fragments, hybrid antibodies, humanised antibodies and single-chain domain antibodies. For brevity, the term "antibody" is used hereafter to refer to said ligand.

DESCRIPTION OF THE PREFERRED EMBODIMENTS

Figure 1A:
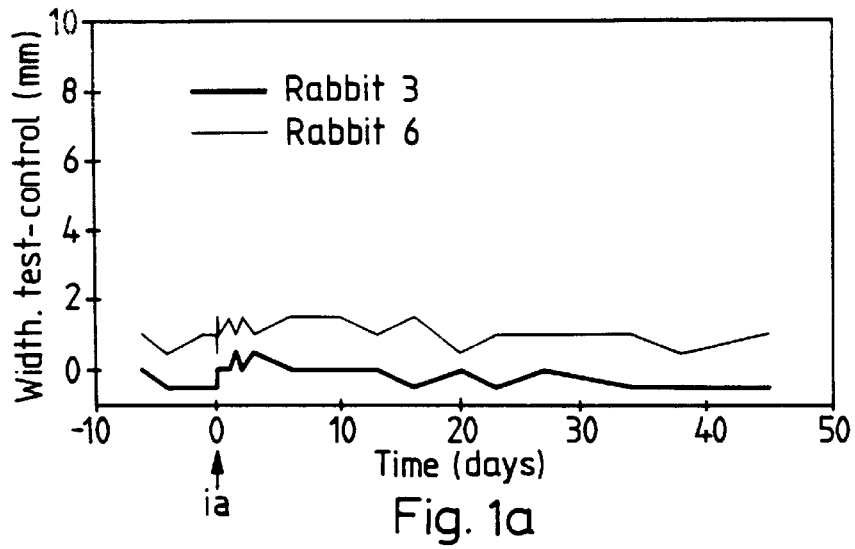
FIG. 1 shows the results of an experiment to determine the causative agent of joint erosions in rabbits, in which (A) shows the results for IgA injected rabbits, (B) shows the results for synovial fluid injected rabbits and (C) shows the results for IgA-$\alpha_1$AT injected rabbits.
Figure 1B:
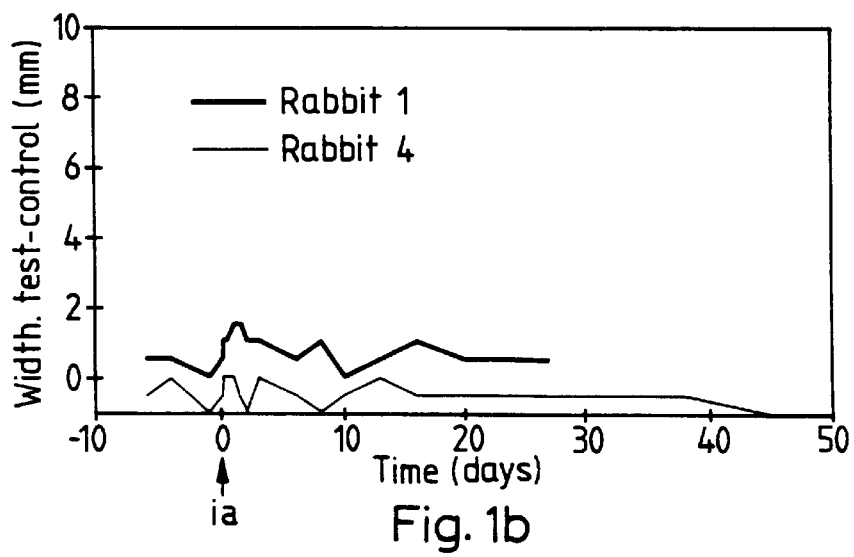
Figure 1C:
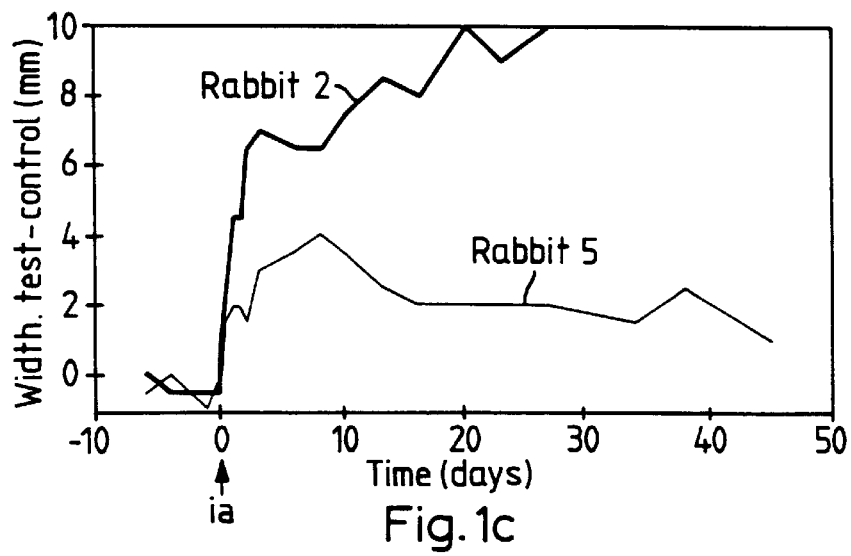

The peptides of the invention are those in which there is a thiol-active cysteine residue and at least two positively charged amino acids. For convenience in this specification, both the one-letter code and the three-letter code for amino acids are used when discussing peptides. The one-letter code and three-letter code is shown below.

| Amino acid | Three-letter Symbol | One-letter Symbol |
|---|---|---|
| Alanine | Ala | A |
| Arginine | Arg | R |
| Asparagine | Asn | N |
| Aspartic acid | Asp | D |
| Asn and/or Asp | Asx | B |
| Cysteine | Cys | C |
| Glutamine | Gln | Q |
| Glutamic acid | Glu | E |
| Gln and/or Glu | Glx | Z |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Among the 20 commonest amino acids, the positively charged amino acids are those which are basic and are arginine, lysine or histidine. Negatively charged amino acids are those which are acidic and are aspartic acid and glutamic acid. Neutral amino acids do not carry an overall positive or negative charge and are the remaining amino acids. Of course, uncommon amino acids or derivatives of common amino acids could alternatively be employed in place of the 20 commonest.

The thiol-active cysteine residue together with at least two positively charged amino-acid residues may conveniently be represented by the following general formula

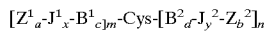
$$[Z^1_a\text{-}J^1_x\text{-}B^1_c]_m\text{-}Cys\text{-}[B^2_d\text{-}J_y^2\text{-}Z_b^2]_n$$

wherein m is 0 or 1, n is 0 or 1 and m+n is 1 or 2;

$J^1$ and $J^2$ represent sequences of positively charged amino acid residues;

$Z^1$, $Z^2$, $B^1$ and $B^2$ represent sequences of residues of positively charged, negatively charged or neutral amino acid residues or sequences of any mixture of postively charged, negatively charged or neutral amino acid residues;

x=0 or 1, y=0 or 1 and x+y=1 or 2;

c=0–4, d=0–4, a=0–18 and b=0–18 with the proviso that when m=0 at least one of $B^2$ and $Z^2$ is a positively charged amino acid residue and when n=0 at least one of $Z^1$ and $B^1$ is a positively charged amino acid residue, and when m=n=1 and y is 0 at least one of $Z^1$, $B^1$, $B^2$, and $Z^2$ is a positively charged amino acid residue and when m=n=1 and x=0 at least one of $Z^1$, $B^1$, $B^2$ and $Z^2$ is a positively charged amino acid residue. $B^1$ and $B^2$ may also represent a non-peptide spacer arm of a length equivalent to that determined by the length of b and c residues of amino acids.

The peptides of the invention are preferably short chain peptides which are capable of preventing the formation of or dissociating already formed IgA-$\alpha_1$AT complex and are particularly useful for the prevention or treatment of RA. They are effective since they are capable of interacting with cysteine residues within the thiol-active IgA and thus preventing $\alpha_1$AT binding or dislodging $\alpha_1$AT already bound.

The peptides must include sufficient amino acid residues on one or both sides of the thiol-reactive cysteine residues to ensure that the resultant peptide will form a mixed disulphide with thiol-reactive (rheumatoid) IgA which thus stabilises the immunoglobulin in an essentially native configuration and does not allow its covalent complexing to $\alpha_1$-antitrypsin.

The peptides also must also be capable of dissociating IgA-$\alpha_1$AT complex which has already formed. The length of the peptide is between 3 and 20 amino acid residues in length, more preferably between 4 and 10 and even more preferably between 4 and 7 residues in length.

The shorter peptides are preferred since there is a minimal risk of the host mounting an immune response against the peptide of the invention.

The number of positively charged amino acid residues in the peptide of the invention is at least two. They may be located on (but not necessarily adjacent to) the N-terminal of the thiol-reactive cysteine, on (but not necessarily adjacent to) the C-terminal of the thiol-reactive cysteine or on (but not necessarily adjacent to) both the N- and C-terminals of the thiol-reactive cysteine residue and when on the same side of the cysteine residue the two positive charges need not be next to each other. When the two positively charged amino acid residues are both located on either the N-terminal or C-terminal of the cysteine residue, the N-terminal is preferable. More preferably, the positive charged amino acid residues are on both the N- and C-terminal of the thiol-active cysteine residue.

The positively charged residues may be directly adjacent to the thiol-active cysteine residue or separated therefrom by a spacer arm and where the peptide comprises positively charged amino acid residues on both the N- and C- terminal sides of the thiol-active cysteine residues, there may be a spacer arm on either the N-terminal side, the C-terminal side or both the N- and C-terminal sides of the thiol-active cysteine residue and may be of different lengths. This spacer arm is designated $B^1$ and $B^2$ in the general formula. $B^1$ and $B^2$ are preferably amino acid residues and are 1–4 amino acid residues in length and $B^2$ is preferably 1–3 residues in length. The amino acids found in the spacer arm may be positively charged, negatively charged, of neutral charge or a mixture of any positively charged, negatively charged or neutral amino acid residues. Preferably, the amino acids in the spacer arm are not cysteine. More preferably the amino acids are of neutral charge and even more preferably are glycine. More preferably, the positively charged amino acid residues are directly adjacent to the cysteine residue on the N-terminal, the C-terminal or both the N- and C-terminals.

Preferred peptides are those which consist of or include (i) residues 231–233 of $\alpha_1$AT or analogues thereof, i.e. His-Cys-Lys where, in the above general formula, m=1, n=1, c=d=0, x=y=1 or (ii) residues 232–234 of $\alpha_1$AT or analogues thereof, i.e. Cys-Lys-Lys where, in the above general formula m=n=1, d=1, y=1. More preferably, the peptides comprise at least the residues 231–234 of $\alpha_1$AT or analogues thereof, i.e. His-Cys-Lys-Lys (SEQ ID NO:1), where in the above general formula m=1, n=1, c=0, 1, d=1, x=1, y=2.

Preferred sequences representative of human $\alpha_1$AT sequences may be elongated so as to incorporate residues 227–237 of $\alpha_1$AT or analogues thereof, i.e. Phe-Asn-Ile-Gln-His-Cys-Lys-Lys-Leu-Ser-Ser (SEQ ID NO: 2) wherein m=1, n=1, c=0, x=1, a=4, d=1, y=1 and b=3.

The peptide of the invention is preferably amidated at the C-terminal. The effect of this amidation is to prolong the half-life of the peptide, thus enabling shorter peptides to be used, and increasing the anti-rheumatic activity. Preferably where the N-terminal is a positively charged amino acid residue the N-terminal is not acylated.

Mixtures of D and L amino acids may be used, or the peptide may exculsively contain D-residues or exclusively contain L-residues.

The antibodies for use in RA therapy comprise an antibody domain specific for an antigenic determinant of a complex of human IgA and human $\alpha_1$AT (IgA-$\alpha_1$AT). The said antibody domain is relatively non-reactive with free human IgA and free$\alpha_1$AT. The complex of IgA and $\alpha_1$AT (IgA-$\alpha_1$AT) is the naturally occurring complex found in analytes taken from patients suffering from rheumatoid arthritis. Most preferably, but as exemplified below, not necessarily, the antibody comprises a monoclonal antibody raised against such a complex. The most preferred monoclonal antibodies are obtainable from hybridomas which are the subject of patent deposits described herein below. Polyclonal antibodies raised against the purified, naturally occurring, complex were not found to be specific for the IgA-$\alpha_1$AT complex, the resulting antisera reacting also with uncomplexed IgA and $\alpha_1$AT.

Alternatively, the antibody can be one raised against a synthetic peptide which is a covalently linked conjugate of short chain peptides representative of those parts of the IgA heavy chain and $\alpha_1$AT chain sequences which comprise an IgA-$\alpha_1$AT complex-specific immunogenic derminant. In a particular embodiment, the first peptide fragment has an amino acid sequence found in the Fc region of human IgA or an analogue of said sequence, and a second peptide fragment has an amino acid sequence found in human $\alpha_1$AT or an analogue of said sequence, which are covalently bound to one another. The preferred form of covalent bonding is an S—S linkage which preserves the immunogenic three dimensional conformation of the linkage of the penultimate cysteine residue, relative to the C-terminal end of human IgA, in the Fc region of human IgA to human $\alpha_1$AT.

Examples of preferred antibodies and synthetic peptides which can be used to raise the antibodies described above have been given in UKPA 9111215.1, which is directed towards monoclonal antibodies specific for IgA-$\alpha_1$AT complex and the use of the said antibodies in a method of diagnosis of RA. The most preferred antibodies have been deposited at the European Collection of Animal Cell Cultures, Porton Down, Salisbury, Wiltshire, England on 6th Feb. 1990 under the accession number ECACC 90020611, hereinafter designated NLW.54 and 13th Dec. 1990 under the accession number ECACC 90121302 hereinafter designated NLW.50. NLW.50 is the most preferred antibody. The deposits were made under the provisions of the Budapest Treaty on the International Recognition of the Deposit of Microorganisms for the Purposes of Patent Procedure.

The preparation of an antibody for RA treatment can be carried out by administering the immunogen, preferably the IgA-$\alpha_1$AT complex, preferably using an adjuvant, to mammals, e.g. rabbits, guinea pigs or mice, bleeding the animals after about one month and thence isolating the resultant antiserum. Improved titres can be obtained by repeated injections over a period of time.

The antibodies include human and murine monoclonal antibodies and Fab' and F(ab')$_2$ fragments thereof. Preferably, the antibody is humanised so as to minimise any adverse reaction to the foreign animal immunoglobulin.

The antibodies can be humanised, for example following the technique described in EPA 0239400 (Winter) wherein only the variable complementary determining regions are foreign to the human body.

The peptides and antibodies may be used both prophylactically and therapeutically. UKPA 9111215.1 (NRDC) describes a method of diagnosing patients suffering from RA as opposed to other diseases which may manifest themselves with similar symptoms. This method may also be used to detect RA in patients who have not yet developed joint erosions (so called "early" RA patients). This method measures the amount of circulating IgA- $\alpha_1$AT complex. By the constant monitoring of early RA patients, therefore, the normal level of complex in that individual can be ascertained, and the amount of peptide administered calculated accurately, depending on the level of circulating complex above a normal value in a particular patient. The peptides and/or antibodies in early RA patients are preferably administered prophylactically (i.e. to prevent formation of elevated levels of IgA- $\alpha_1$AT complex). In patients who have developed joint erosions already, it is too late for prophylactic administration of peptides and/or antibodies and thus they are administered in a therapeutic sense, the dosages depending on the level of complex found circulating in those patients, and the value considered normal for that particular patient as determined by knowledge of what was his "normal" level of complex before RA developed, or at what concentration of complex are the symptoms of RA alleviated.

The peptides and antibodies for use in therapy may be formulated with a physiologically acceptable diluent or carrier for use as pharmaceuticals for human use by a variety of methods. They may for instance be incorporated into a form suitable for injection or infusion and are therefore conveniently sterile and pyrogen free. They may also more preferably be incorporated into a form suitable for oral administration either as a liquid or solid.

Therefore, according to a second aspect of the invention there is provided a pharmaceutical composition comprising a peptide or antibody as described hereinbefore together with a physiologically acceptable diluent or carrier.

The peptides and/or antibodies may be formulated in a form suitable for oral administration and thus may be incorporated into a liquid, diluent or carrier, although it is more usual to use a solid, for example a conventional solid carrier material such as starch, lactose, dextran or magnesium stearate. Such solid compositions may conveniently be of a formed type, for example as tablets, capsules etc.

The antibody and/or peptide is preferably introduced into the host by a parenteral route, preferably by intraarticular injection. Any of the common liquid or solid vehicles may be employed, which are acceptable to the host and which do not have any adverse side effects on the host or any detrimental effects on the vaccine. Phosphate buffered saline (PBS), at a physiological pH, e.g. 6.8 to 7.2, preferably pH 7.0 may be used as a vehicle, alone or with a suitable depot.

The compositions may be formulated in unit dosage form and the amount and frequency of administration being dependent upon the severity of the disease in the individual patient. Constant monitoring of the levels of IgA-$\alpha_1$AT complex for example by the technique described in UKPA 9111215.1 will help to determine the dosage for each particular patient.

The invention will now be illustrated by way of the following Examples.

EXAMPLE 1

SYNTHESIS OF PEPTIDES

Peptides were synthesised using an LKB Biolynx automated peptide synthesiser using standard Fmoc chemistry. All cysteine residues were protected with trityl groups during synthesis. Cleavage and deprotection of the peptide was performed by using a 95% trifluoroacetic acid (TFA), 5% ethane-dithiol mixture. The peptides were then rotor-evaporated to remove the TFA, followed by an ether extraction to remove the ethane dithiol, using several changes of ether and extracting into 0.05M acetic acid. A final clean up of the peptides was then carried out using a Sephadex G10 gel filtration column. Peptides were then freeze dried and stored in a desiccator at 4° C. until used. Before use, all peptides were checked for the presence of free SH by a modified Ellman test as follows.

100 $\mu$l of peptide (0.5 mM) was double diluted using 0.1M phosphate buffer (pH 8.0) in a flexible microtitre plate (Falcon). Cysteine (0.2M) was also double diluted to act as a standard. 25 $\mu$l of 5,5'-dithiobis (2-nitrobenzoic acid), 645 $\mu$g/ml, was then added to each well. Colour was allowed to develop for 15 minutes, and the plate then read at 410 nm in a Multiscan plate reader. A calibration curve was constructed using the cysteine and the free SH for the peptides was calculated.

The following groups 1–6 of peptides were synthesised. For the purposes of showing the effect of the positioning of the at least two positively charged amino acid residues in relation to the thiol-active cysteine residue on the properties of the peptide, and for comparing peptides within the invention having differing sub-generic formulae, it is convenient to define various groups. In the following sub-generic formulae "+" denotes a basic residue, "−" denotes an acidic residue, "r" and "S" denote other amino acid residues (normally but not necessarily glucine).

(a) GROUP 1:+r Cys s+nh$_2$

In this group of peptides, there are positively charged amino acid residues on both the N-terminal or C-terminal of the thiol-active cysteine residue. The peptide may be amidated (represented by "nh$_2$") and the positively charged residues may be separated from the thiol-active cysteine residue by spacer residues, represented by "r" and "s" in the sub-generic formula. According to the general formula of the invention m=n=1, x=y=1, n=0–4, b=0–4.

(b) GROUP 2: Cys r+s+nh2

In this group of peptides, the positively charged amino acid residues are located on the C-terminal of the thiol-active cysteine residue. According to the general formula of the invention.
m=0, n=1, d=0–4 (as represented by "r"), b=1–5 (as represented by "s+" where s=0–4) y=1

(c) GROUP 3:+r+s Cys nh$_2$

In this group of peptides the positively charged amino acid residues are located on the N-terminal of the thiol-active cysteine residue. According to the general formula m=1, n=0, x=1, c=0–4 (as represented by s) a=0–5 (as represented by "+r" where r=0–4).

(d) GROUP 4: r His Cys Lys Lys nh$_2$ (SEQ ID NO:3)

The peptides in this group all have as a "core" the sequence His Cys Lys Lys. According to the general formula the core is m=n=1, c=d=0, x=1, y=1, a=0 and b=1. Additionally, peptide is elongated at the N-terminal by residue or residues "r". The effect of the presence of negatively charged residues is investigated.

(e) GROUP 5: His Cys Lys Lys s nh$_2$ (SEQ ID NO:3)

The peptides of group 5 are as group 4 except the peptide is elongated at the C-terminal by residue or residues "s". Again, the effect of negatively charged residues is investigated.

(f) GROUP 6

Various control peptides and peptides which although conforming to the general formula of the invention did not fit the above sub-generic formulae, for example being non-amidated.

EXAMPLE 2

PREPARATION OF IgA-α$_1$AT COMPLEX

IgA myeloma (Brierley) plasma was defibrinated by the addition of thrombin (10 IU/100 ml plasma). The plasma was then stirred overnight at 4° C. and the resulting fibrin clot removed, to give serum. Saturated ammonium sulphate was added dropwise with constant stirring to the serum to a final concentration of 50% at 4° C. The mixture was then centrifuged in an MSE Coolspin 2 at 3000 rpm for 15 minutes at 4° C. The resulting precipitate was then redissolved in ultra-pure water and dialysed against several changes of phosphate buffered saline, pH 7.2 (PBS). The sample was then applied, at 4° C., to a Sephacryl S300HR gel filtration column, equilibrated with PBS, and the protein fractions collected, using PBS as the buffer during the separation. Column fractions were assayed for the presence of IgA-α$_1$AT using the ELISA technique with plates pre-coated with anti IgA-α$_1$AT . Complex-positive fractions were pooled and concentrated using an Amicon Centri-prep concentrator. The complex-rich fractions were then added, at 4° C., to a Sephacryl S200HR gel filtration column and using the ELISA technique, IgA-α$_1$AT positive fractions were collected. Fractions were concentrated as before. Purity was confirmed by HPLC, SDS-PAGE and 2-dimensional electrophoresis.

EXAMPLE 3

IN VIVO STUDIES (a) Methods of inducing rheumatoid arthritis in rabbits (i) Active Model Active models of RA may be set up in rabbits by the classical Dumonde D. C.—Glynn L. G. procedure (British Journal of Experimental Medicine, 1962, 43 p373) or by a variation of this method which involves the use of altered self-IgG as the arthritogen to initiate the formation of rheumatoid factor not seen in the classical model, (Galloway et al., Immunology, 1983, 49, 511). An alternative method described below was carried out.

Rabbits were injected subcutaneously (sc) with 5 mg ovalbumin (OA) in 0.5 ml sterile saline emulsified in 0.5 ml complete Freunds adjuvant (CFA) in 3 separate sites in the scruff of the neck. 14 days later a dose of 5 mg OA in 0.5 ml sterile saline emulsified in incomplete Freunds adjuvant (IFA) was injected subcutaneously into 3 sites in the scruff of the neck. After a further 10 days the animals were tested for a delayed hypersensitivity response by the intradermal injection of OA (100 μl) at 500, 200, 100 mg/ml in sterile saline, with sterile saline used as a negative control. After 24 hrs. the sites of injection were examined and any swelling and redness assessed. All animals that had a negative response (no visible swelling and little or no redness) were given another injection (subcutaneously) of 5 mg OA in sterile saline emulsified in 0.5 ml IFA. 7 days later, arthritis was induced by the intra-articular injection of 10 mg OA In 0.5 ml sterile saline into the right knee joint, 0.5 ml of sterile saline being injected into the left knee joint as a negative control. The degree of swelling was monitored by the measurement of knee width, using calipers.

(ii) Passive Model

Arthritis was induced in groups of rabbits by the injection of isolated IgA-α$_1$AT complex into their knee joints. IgA-α$_1$AT complex was purified by the method described in Example 2. This results in the rapid development of chronic arthritis in the rabbits. This system has two advantages over the active model, firstly, the speed of RA development and secondly the knowledge that the RA has been induced by the IgA-α$_1$AT complex itself. This is demonstrated as follows:

Pairs of normal rabbits were injected intra-articularly (ia) with 0.5 ml saline (negative control) in one joint and 0.5 ml test substance (IgA, IgA-α$_1$AT complex or synovial fluid (SF) which was negative for IgA-α$_1$AT complex but high in α$_1$AT) in the other. The progression of RA was monitored by measuring the joint width using callipers, comparing the control and test substance injected joints, (FIGS. 1a, b and c).

At the end of the experimental period the joints were examined macroscopically and histopathalogically. Macroscopically the IgA and SF injected joints had a normal appearance, no swelling visible, the supra and infra patella fat pads were white with no overgrowth of patella by fat pads, whereas the IgA-α$_1$AT complex injected animals were visibly swollen and the fat pads were brown (indicating cellular infiltration) enlarged and overgrowing the patella and crusiate ligaments. The histopathology showed cellular infiltration into the fat pads, increased number of cells in the synovium lining layer, villus formation, overgrowth of the patella and destruction of the proteoglycan in the patella. All changes seen in the IgA-$\alpha_1$AT complex-injected animals were consistent with a rheumatoid arthritis-type of disease.

(b) Measuring the anti-rheumatic potential of the peptides in passive model of RA Normal rabbits were injected intra-articularly (ia) with either 0.5 ml saline in the left knee as negative control, or 0.5 ml purified IgA-$\alpha_1$AT complex in the right knee to induce the arthritis. This induced an immediate arthritis which was monitored by measuring the joint width with callipers. 48 hours after the induction of the arthritis, 0.1 ml of a 10 mg/ml solution of the peptide His-Cys-Lys-Lys, representing amino acids 231–234 of $\alpha_1$AT were injected ia. As a negative control other animals were treated with oral lactose. This was repeated at 2–3 day intervals over the test period. After 14 days the animals were sacrificed and joint sections taken for later histological examination.

| Day 0 | saline (left knee), IgA-$\alpha_1$AT (right knee) |
|---|---|
| Day 2 | peptide (right knee) |
| Day 4 | " |
| Day 7 | " |
| Day 9 | " |
| Day 11 | " |
| Day 14 | animals sacrificed |

Figure 2:
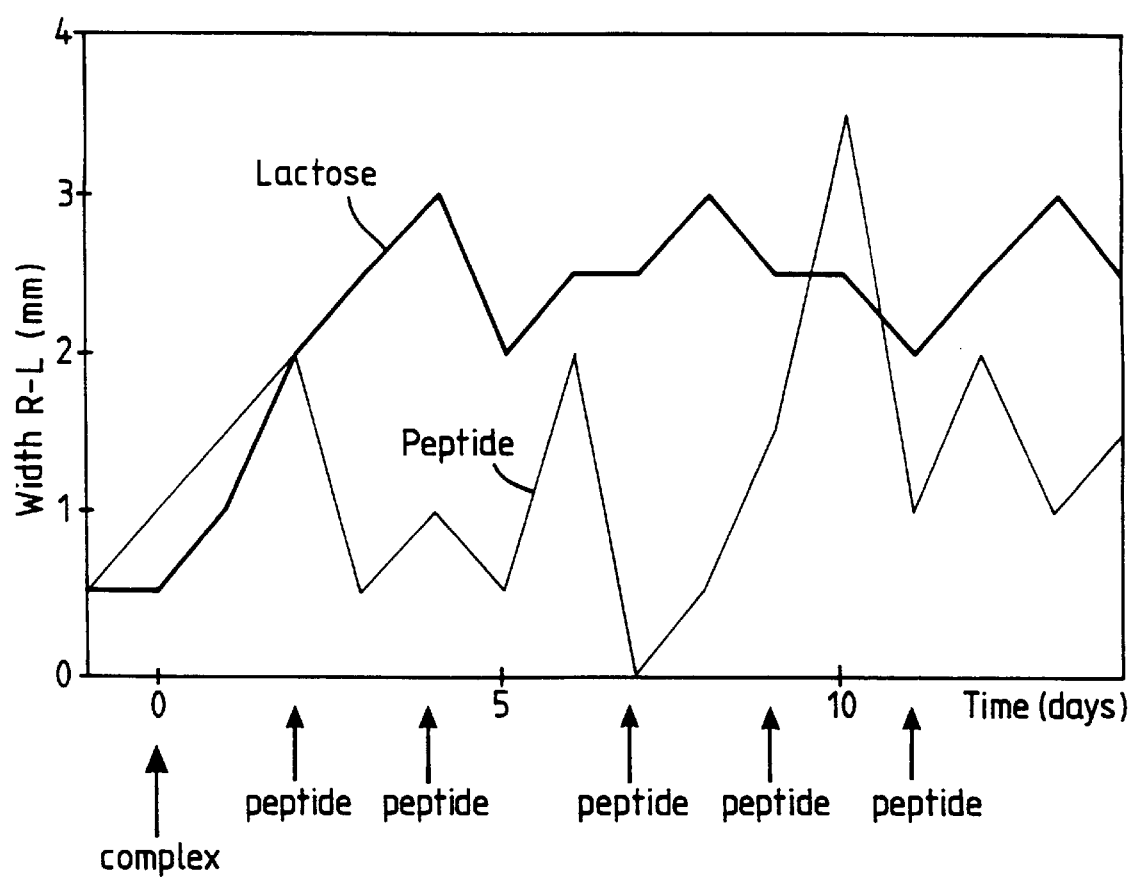
FIG. 2 shows the results of an experiment in which either a peptide of the invention or a placebo was administered to arthritic rabbits.

The results are shown in FIG. 2.

Statistical (t-test) analysis of the data revealed a significant decrease of swelling of the joints of the peptide injected group on two different occasions throughout the treatment period (i.e. days 1 and 11 after start of treatment); by comparison with the size of joints of animals in the negative control group (treated with placebo).

EXAMPLE 4

IN VITRO STUDIES OF ANTI-RHEUMATIC ACTIVITY OF SYNTHETIC PEPTIDES

The ability of the peptides of the invention to dissociate purified IgA-$\alpha_1$AT complex in vitro was tested as described below. The anti-rheumatic drug D-penicillamine and other synthetic peptides were used as controls.

(a) HPLC ANALYSIS

50 $\mu$l of a 57 $\mu$g/ml solution of purified IgA-$\alpha_1$AT complex was incubated with an equal volume of peptide or drug (500 $\mu$M) for 90 minutes at 37° C. 25 $\mu$l of the incubated mixture was then applied to a 30 cm long TSK G3000 SWXL HPLC column. The sample was monitored at wavelength 206 nm at a flow rate of 1 ml/minute with phosphate buffer (0.1M) pH 7.1.

The results are shown in the column headed "HPLC minimum" in Tables 1–6 below. They represent the ability of the peptides to dissociate the IgA-$\alpha_1$AT complex in vitro.

In these experiments, the base-lines level comprises a complex: free IgA ratio of 14%. The minimum concentration of peptide taken to produce a positive dissociation effect is that which results in a complex: free IgA ratio at 20%. In the results tables, all the peptide values are expressed in $\mu$Moles. Peptide values at >500 $\mu$M are taken to indicate that no complex dissociation occurred at the highest peptide concentration tested.

(b) INHIBITION OF C3-ACTIVATION

Various peptides were tested for their ability to prevent the IgA-$\alpha_1$AT complex from activating the alternative complement (C3) pathway.

The method of measuring the capacity to activate the alternative complement pathway by the non-immune IgA-$\alpha_1$AT complex and the subsequent inhibition of this activation by anti-rheumatic peptides is described below.

This method was based on the method described by Riches and Stanworth, Immunology Letters, 1980, 1, 363, 366, with modification to miniaturise it thus allowing the assay to be carried out on microtitre plates.

The initial observation by Platts-Mills and Ishizaka (J Immunol. (1974) 113, 348,358) that low dilutions of fresh normal human serum, from which calcium had been removed by chelation with 10 mM EGTA to block the classical complement pathway, caused greater than 90% haemolysis of unsensitised rabbit erythrocytes when incubated at 37° C. was employed in this assay.

The non-immune complex IgA-$\alpha_1$AT had been shown in the past to be the only known soluble complex to activate the alternative pathway complement and inhibit the lysis of the rabbit erythrocytes. This inhibition required biologically active complex. Complex isolated from 10 year old IgA myeloma plasma was found to be unable to activate alternative complement and hence was not biologically active.

Buffers Required

The buffers solutions required in this assay were (a) Total lysis buffer (1% Triton100 in ultra pure water), (b) Alternative pathway complement fixation diluent (APCFD) which was:

83 volumes CFD, DH 7.2 (1 oxoid tablet: 100 ml UPW)
10 volumes 0.1M EGTA pH 7.2
7 volumes MgCl$_2$ pH 7.2

This buffer was also prepared in a double concentrated form, and (c) cell storage buffer (0.1M citrate buffer pH 6.2).

Serum

Blood was obtained by venipuncture from a healthy human individual. The blood was allowed to clot for 1 hour at room temperature and then stored overnight at 4° C. The serum was removed and stored at -70° C. in 1 ml aliquots. For use, the serum was defrosted and 100 $\mu$l of 0.1 m EGTA pH 7.2 and 70 $\mu$l 0.1 m MgCl$_2$ pH 7.2 was added.

Rabbit Red Blood Cells

Rabbit red blood cells (RBC) were obtained by venipuncture of a healthy rabbit and collected into 0.1M citrate buffer pH 6.2. The RBC were washed 3 times in citrate buffer and the cells were stored in this buffer which was changed every week. It was possible to store cells in this way for 3 weeks.

Peptides

The peptides were synthesised as described in Example 1 and made up in UPW to 1 mM. They were kept frozen at -70° C. prior to use.

IgA-$\alpha_1$AT Complex

This was prepared as previously described in Example 2. It was kept frozen in small aliquots prior to use.

METHOD OF PERFORMING THE ASSAY (i) Estimation of dilution of serum needed to just lyse 100% of Rb RBC Using a round bottomed welled flexible microtitre plate 100 $\mu$l neat serum (with added EGTA and MgCl$_2$) was added to the first wells in duplicate. This was double diluted out, with APCFD to give a volume of 50 $\mu$l well. 8 test wells (+duplicates) were sufficient.

8 wells were prepared as a positive control—(100 $\mu$l 1% Triton/UPW).

8 wells were prepared as a negative control—(100$\mu$l APCFD (Blank)).

50 $\mu$l of APCFD was added to the test wells and 50$\mu$l of 1% rabbit RBC was added to all wells. The plate was then incubated at 37° C. for 30 minutes and then centrifuged for 10 minutes at 2000 rpm.

75 μl of the supernatant was carefully removed and plated onto a flat bottom welled microtitre plate. The plates were then read at 410 nm interference, 690 nm reference. The zero or blank value was calculated as the mean value of negative control wells and using the mean of the positive control wells, the percentage lysis for serum dilutions was calculated. In future assays the serum dilution in which lysis was approx. 80% of Rb RBC was used. This was usually in the range 1:4–1:6 dilution (ie. 1 ml serum: 4 ml APCFD–6 ml APCFD).

(ii) Using IgA-$\alpha_1$AT complex as an alternative complement pathway inhibitor A 1:1 dilution of IgA-$\alpha_1$AT complex was made with twice concentrated APCFD. 100 μl of this 1:1 dilution of complex was added to the first wells in duplicate. This was double diluted out with APCFD to give 50 μl per well. 50 μl of the predetermined dilution of serum (see (i) above) was added to each well. Positive and negative control wells as described in (a) above and wells containing serum alone were used as controls. The plates were incubated at 37° C. for 30 minutes and then centrifuged at 2000 rpm for 1 minute. 50 μl of 1% rabbit red blood cells were added to each well and the plates were incubated again at 37° C. for 30 minutes. The plate was then re-centrifuged at 2000 rpm for 10 minutes. 75 μl of the supernatant was removed from each well and plated on to a flat bottomed welled microtitre plate which was read at 410 nm interference 690 nm reference.

The control wells were checked to ensure that the dilution of serum used had lysed the rabbit RBC to a significant amount. Then, the % inhibition of the mean values for the complex dilutions were calculated with respect to the serum control wells. This enabled a suitable concentration of IgA-$\alpha_1$AT complex to be determined for the next stage of the assay. A suitable concentration was in the range 1:1–1:4 complex: APCFD.

(iii) Use of putative anti-rheumatic peptides as inhibitors of complex inhibition of alternative pathway complement lysis of Rabbit RBC The peptides (500 μM concentration) were diluted 1:1 with the double concentrated APCFD. These solutions of peptides were then double diluted down a round bottomed welled microtitre plate, such that there was 25 μl of peptide solution per well. Positive and negative controls, serum only controls and serum plus IgA-$\alpha_1$AT complex controls were included in the assay. 25 μl of a suitable dilution of IgA-$\alpha_1$AT complex (see (iii) above) was added to the test wells and the plates were centrifuged at 2000 rpm for 1 minute. The plates were then incubated at 37° C. for 1½ hours. 50 μl of a suitable serum dilution (see (a) above) was added and the plates centrifuged at 2000 rpm for 10 minute, then incubated at 37° C. for 30 minutes. 50 μl of 1% rabbit RBC was added and after a further 30 minutes of 37° C. incubation, the plates were centrifuged at 2000 rpm for 10 minutes. Supernatants were taken as previously.

Interpretation of Results

The mean values of each of the serum(s), serum and complex (c+s) and total haemolysis wells were calculated. The % haemolysis with respect to lysis by serum wells was calculated. The peptide was considered to have titred out when % lysis value was equal to the calculated % lysis value given by the c+s mean. The titre point for the peptide was calculated as the concentration in μM of the peptide that just gave greater lysis than the c+s mean value.

The results are shown in Tables 1–6 below. The results are expressed as the minimum concentration of peptide needed to prevent C3 activation, and are found in the column headed "C'".

(c) MACROPHAGE INHIBITION ASSAY

A mouse macrophage cell line (PU 518) was stimulated to release lysosomal enzymes by the addition of purified human IgA-$\alpha$1AT complex. The degree to which this release was then inhibited by the peptides or other drugs was investigated, with the degree of inhibition being indicative of activity; the concentration of peptide or other test drugs giving 50% inhibition being recorded. Briefly the method was as follows:

25 μl of peptide or drug was double diluted in RPMI 1540+10% foetal calf serum (FCS) in a sterile tissue culture 96 well plate. 25 μl of IgA-$\alpha_1$AT complex in RPMI 1640+ 10% FCS at about 0.2 mg/ml was then added to all wells. 50 μl of cells at a concentration of $2 \times 10^6$ cells/ml in RPMI 1640+10% FCS was then added to each well.

Control wells of cells alone and cells+IgA-$\alpha_1$AT complex were also prepared. The plate was then gently mixed and incubated overnight (16hr) at 37° C. in a 4% $CO_2$ atmosphere. Plates were then centrifuged at 1200 rpm for 10 minutes in a bench top centrifuge.

40 μl of supernatant was then taken from each well and added to a 96 well polystyrene assay plate, to which was added 40 μl of 160 mM acetate buffer (pH 4.3) containing 2 mM phenolphthalein-β-D-glucorinic acid. To obtain a standard curve, dilutions of phenolphthalein in acetate buffer from 100–5 μg/ml were also added to separate wells in the assay plate.

The plates were then incubated at 37° C. for 4 hours before 150 μl of 0.2M glycine/NaOH buffer (pH 10.6) containing 0.2M NaCl was added to stop the reaction.

Plates were then shaken for 3 minutes before the optical density at 570 nm was read on a plate reader, and the amount of β-D-glucoronic acid released from the cells calculated. The concentration of peptide or drug giving 50% inhibition of release was then noted.

The results for the macrophage inhibition assays are expressed as the concentration needed to prevent 50% release of β-glucoromidase.

The results of these experiments are tabulated in Tables 1–6 below.

TABLE 1

GROUP 1 PEPTIDES

| Sequence | r | s | Peptide number (for Ref) | HPLC % | C' (μM) | Macrophage 50% Inhibition (μM) |
|---|---|---|---|---|---|---|
| HCKnh$_2$ | 0 | 0 | 116 | 125 | 62 | |
| HCKKnh$_2$ | 0 | 1 | 132 | 10 | 16 | 60 |
| HCGKnh$_2$ | 0 | 1 | 141 | 50 | 8 | 100 |
| KCGKnh$_2$ | 0 | 1 | 177 | 50 | 62 | 250 |
| RCGKnh$_2$ | 0 | 1 | 139 | 10 | 62 | |
| HCGGKnh$_2$ | 0 | 2 | 142 | 50 | 16 | 500 |
| HCGGGKnh$_2$ | 0 | 3 | 143 | 125 | 32 | 150 |
| HCGGGGKnh$_2$ | 0 | 4 | 160 | 50 | 4 | 90 |
| HGCKnh$_2$ | 1 | 0 | 161 | 10 | <2 | 100 |
| HGCGnh$_2$ | 1 | 1 | 144 | 50 | 32 | |
| HGCGGKnh$_2$ | 1 | 2 | 166 | 10 | <2 | |
| HGCGGGKnh$_2$ | 1 | 3 | 167 | 10 | <2 | |
| HGCGGGGnh$_2$ | 1 | 4 | 168 | 10 | 8 | |
| HGGCKnh$_2$ | 2 | 0 | 164 | 50 | 8 | |
| HGGCGKnh$_2$ | 2 | 1 | 145 | 50 | 32 | 30 |
| HGGCGGKnh$_2$ | 2 | 2 | 162 | 10 | <2 | |
| HGGCGGGKnh$_2$ | 2 | 3 | 169 | 50 | 8 | |
| HGGCGGGGKnh$_2$ | 2 | 4 | 161 | 10 | <2 | 100 |
| HGGGCKnh$_2$ | 3 | 0 | 165 | 50 | <2 | |
| HGGGCGKnh$_2$ | 3 | 1 | 146 | 50 | 32 | |

TABLE 1-continued

GROUP 1 PEPTIDES

| | r | s | Peptide number (for Ref) | HPLC % ($\mu$M) | C' ($\mu$M) | Macrophage 50% Inhibition ($\mu$M) |
|---|---|---|---|---|---|---|
| HGGGCGGKnh$_2$ | 3 | 2 | 171 | 50 | 4 | |
| HGGGCGGGKnh$_2$ | 3 | 3 | 163 | 50 | <2 | |
| HGGGCGGGGKnh$_2$ | 3 | 4 | 172 | 50 | 4 | |
| HGGGGCKnh$_2$ | 4 | 0 | 159 | 10 | 8 | |
| HGGGGCGKnh$_2$ | 4 | 1 | 158 | 50 | 16 | |
| HGGGGCGGKnh$_2$ | 4 | 2 | 173 | 50 | 4 | |
| HGGGGCGGGKnh$_2$ | 4 | 3 | 174 | 125 | 4 | 125 |
| HGGGGCGGGGKnh$_2$ | 4 | 4 | 175 | 125 | 2 | |
| HDCKKnh$_2$ | 1 | 1 | 198 | 10 | 3.9 | |
| HYCKKnh$_2$ | 1 | 1 | 199 | 10 | 3.9 | |
| HPCKKnh$_2$ | 1 | 1 | 201 | 10 | 3.9 | |
| HECKKnh$_2$ | 1 | 1 | 204 | 10 | <1.95 | |
| HFCKKnh$_2$ | 1 | 1 | 208 | 10 | 3.9 | |
| HFCKKnh$_2$ | 1 | 1 | 209 | 10 | 3.9 | |

The results show that it is possible to increase the number of spacer residues r and s without having any appreciable effect on activity until at least 4r and 3s residues are reached. Although glycine is the preferred amino acid spacer, the results show that any amino acid including those having a negative charge are also suitable.

TABLE 2

GROUP 2 PEPTIDES

| Sequence | r | s | Peptide number(s) | HPLC % minimum ($\mu$M) | C' minimum ($\mu$M) | Macrophage 50% Inhibition |
|---|---|---|---|---|---|---|
| CKKnh$_2$ | 0 | 0 | 114 | 125 | >1250 | |
| CHGKnh$_2$ | 0 | 1 | 176 | >500 | 125 | |
| CHGGKnh$_2$ | 0 | 2 | 148 | 125 | 32 | |
| CHGGGKnh$_2$ | 0 | 3 | 186 | >500 | >250 | 250 |
| CHGGGGKnh$_2$ | 0 | 4 | 187 | 50 | 62 | |
| CGHKnh$_2$ | 1 | 0 | 183 | >500 | >250 | |
| CGGHKnh$_2$ | 2 | 0 | 184/189 | >500/50 | >250 | |
| CGGGHKnh$_2$ | 3 | 0 | 185 | >500 | 250 | |
| CGGGGHKnh$_2$ | 4 | 0 | 188 | >500 | 62 | 1000* |

(*Promotes enzyme release)

There is some anti-complex activity but not as high a level as for Group 1 peptides.

TABLE 3

GROUP 3 PEPTIDES

| Sequence | r | s | Peptide number(s) | HPLC % minimum ($\mu$M) | C' minimum ($\mu$M) | Macrophage 50% inhibition ($\mu$M) |
|---|---|---|---|---|---|---|
| HKCnh$_2$ | 0 | 0 | 178 | 10 | 16 | 200 |
| HKGCnh$_2$ | 0 | 1 | 182 | 50 | 8 | |
| HKGGCnh$_2$ | 0 | 2 | 191 | 50 | <2 | |
| HKGGGCnh$_2$ | 0 | 3 | 192 | 50 | <2 | |
| HKGGGGCnh$_2$ | 0 | 4 | 193 | 50 | <2 | 30 |
| HGKCnh$_2$ | 1 | 0 | 179 | 50 | 8 | |
| HGGKCnh$_2$ | 2 | 0 | 180 | 50 | 4 | |
| HGGGKCnh$_2$ | 3 | 0 | 194 | 50 | <2 | |
| HGGGGKCnh$_2$ | 4 | 0 | 195 | 50 | <2 | 200 |
| HGKGCnh$_2$ | 1 | 1 | 181 | 50 | 32 | 500 |

This group of peptides have high anti-complex activity.

TABLE 4

GROUP 4 PEPTIDES

| Sequence | r | Peptide number(s) | HPLC ($\mu$M) | C' ($\mu$M) | macrophage 50% inhibition ($\mu$M) |
|---|---|---|---|---|---|
| DHCKKnh$_2$ | 1 | 113 | 10 | 78 | 70 |
| EHCKKnh$_2$ | 1 | 154 | 5 | <2 | |
| DGHCKKnh$_2$ | 2 | 119 | 10 | | |
| HKGGGCnh$_2$ | 4 | 192 | 50 | <2 | |
| EGHCKKnh$_2$ | 2 | 155 | 5 | <2 | 60 |
| DGGHCKKnh$_2$ | 3 | 118 | 50 | | |
| DGGHCKKnh$_2$ | 4 | 117 | 10 | 8 | |
| DGGGHCKKnh$_2$ | 5 | 129 | 10 | 32 | 125 |
| DGGGGHCKKnh$_2$ | 6 | 130 | 10 | 16 | |
| dAHCKKnh$_2$ | 1 | 205 | 10 | 1.95 | |
| QHCKKnh$_2$ | 1 | 133 | 10 | 31 | |
| IQHCKKnh$_2$ | 2 | 134 | 10 | 62 | |
| NIQHCKKnh$_2$ | 3 | 135 | 10 | 31 | |
| FNIQHCKKnh$_2$ | 4 | 136 | 5 | 63 | 90 |
| MFNIQHCKKnh$_2$ | 5 | 137 | 5 | 31 | 125 | d denotes D-residues of amino acids

The mixed charge constructs were active.

TABLE 5

GROUP 5 PEPTIDES

| Sequence | s | Peptide number(s) | HPLC ($\mu$M) | C' ($\mu$M) | macrophage 50% inhibition ($\mu$M) |
|---|---|---|---|---|---|
| HCKKDnh$_2$ | 1 | 120 | 50 | 62 | 25 |
| HCKKEnh$_2$ | 1 | 150 | 50 | 8 | |
| HCKKGDnh$_2$ | 2 | 121 | 125 | 62 | |
| HCKKGEnh$_2$ | 2 | 151 | 50 | 16 | |
| HCKKGGDnh$_2$ | 3 | 122 | 50 | 31 | |
| HCKKGGEnh$_2$ | 3 | 152 | 10 | 125 | |
| HCKKGGGDnh$_2$ | 4 | 123 | 50 | 31 | |
| HCKKGGGEnh$_2$ | 4 | 153 | 50 | 63 | |
| HCKKdAnh$_2$ | 1 | 206 | 50 | 31.3 | | d denotes D-residues of amino acids

The mixed charge constructs were active.

TABLE 6

GROUP 6 PEPTIDES

| Sequence | Peptide Number | HPLC minimum ($\mu$M) | C' minimum ($\mu$M) | Macrophage 50% inhibition |
|---|---|---|---|---|
| D-Penicillamine | — | 250 | 31 | 500 |
| Cysteine | — | 250 | 16 | 500 |
| EVDGTCY | 124 | 250 | 16 | |

TABLE 6-continued

GROUP 6 PEPTIDES

| Sequence | Peptide Number | HPLC minimum ($\mu$M) | C' minimum ($\mu$M) | Macrophage 50% inhibition |
|---|---|---|---|---|
| VDGTCY | 125 | 250 | 31 | |
| DGTCY | 126 | >500 | | |
| GTCY | 127 | 50 | | |
| TCY | 128 | 125 | | |
| Substance P | 36 | >500 | >500 | >500 |
| HCKK | 107 | 250 | | |
| HCK | 110 | 500 | | |
| HC | 112 | 250 | | |
| CK | 109 | 500 | | |
| CKK | 106 | 500 | | |
| CKnh$_2$ | 115 | 500 | | |
| Glutathione | — | 500 | 31 | |
| N-acetyl Cysteine | — | 500 | 4 | |
| KTKGSGFFVF | 30 | >500 | 31 | 250 |
| VSVVMAEVDGTCY | 80 | 10 | 16 | |
| IVLVDNKCKCAR | 89 | 50 | 125 | |
| GMFNIQHCKKLSS | 90 | 50 | 31 | |
| HCCGKnh$_2$ | 147 | 10 | 32 | 250 |
| KAAGS | 96 | >500 | | |
| DHCKK | 108 | 10 | | |
| dAHCKKdAnh$_2$ | 210 | 10 | 3.9 | | d denotes D-residues of amino acids

Extension of the core tetrapeptide (His Cys Lys Lys) sequence as in peptides 133–137 had no effect on activity. Smaller versions of the core tetrapeptide His Cys Lys Lys (106, 109, 110, 112, 115) were substantially less active; as was a non-amidated form (107) of the core tetrapeptide. Amongst the control reducing substances tested, glutathione and N-acetyl cysteine were relatively inactive.

We claim:

1. A pharmaceutical composition comprising a prophylactically or therapeutically effective amount of a synthetic peptide consisting of from 3 to 7 amino acid residues or analogue thereof wherein the analogue is at least partly non-peptide in nature comprising a single theol-active cysteine residue and having the following formula:

$$Z^1_a\text{-}B^1_c\text{-}Cys\text{-}B^2_d\text{-}Lys\text{-}Lys\text{-}Z^2_b$$

wherein $Z^1$, $Z^2$, $B^1$ and $B^2$ represent sequences of positively charged, negatively charged or neutral amino acid residues (other than Ser adjacent Cys) or sequences of any mixture of positively charged, negatively charged or neutral amino acid residues (other than Ser adjacent Cys); or $B^1$ and $B^2$ represent non-peptide spacer arms of a length equivalent to that determined by the length of d and c residues of amino acids c=0 to 4, d=0 to 4; and a=0 to 4 and b=0 to 4;

and wherein a positively charged amino acid residue is located on the peptide's N-terminal or C-terminal; the peptide or analogue thereof being capable of preventing the formation of or dissociating already formed 1 ga-$\alpha_1$AT complex, and with the proviso that the peptide does not include the sequences Cys-Ala-Lys-Lys-Ile and Cys-Lys-Lys-Thr-Glu.

2. A composition according to claim 1 wherein d=0 so that the positively charged Lys-Lys residue is directly adjacent the thiol-active cysteine residue.

3. A composition according to claim 1 wherein d≠0 so that the positively charged Lys-Lys residue is separated from the thiol-active cysteine residue by a spacer arm.

4. A composition according to claim 3 wherein the spacer arm comprises 1–4 amino acid residues.

5. A composition according to claim 4 wherein the amino acid residues are neutral amino acid residues.

6. A composition according to claim 5 wherein the neutral amino acid residues are glycine.

7. A composition according to claim 1 consisting of the residues Cys-Lys-Lys.

8. A composition according to claim 1 consisting of the residues His-Cys-Lys-Lys.

9. A composition according to claim 1 which is amidated at the C-terminal.

10. A composition according to claim 1 wherein the peptide is incorporated into a form suitable for injection.

11. A composition according to claim 1 wherein the peptide is incorporated into a form suitable for oral administration.

12. A method of treating rheumatoid arthritis in a patient in need of such treatment, said method comprising the step of administering an effective amount of a synthetic peptide consisting of from 3 to 7 amino acid residues or analogue thereof wherein the analogue is at least partly non-peptide in nature comprising a single thiol-active cysteine residue and having the following formula:

$$Z^1_a\text{-}B^1_c\text{-}Cys\text{-}B^2_d\text{-}Lys\text{-}Lys\text{-}Z^2_b$$

wherein $Z^1$, $Z^2$, $B^1$ and $B^2$ represent sequences of positively charged, negatively charged or neutral amino acid residues (other than Ser adjacent Cys) or sequences of any mixture of positively charged, negatively charged or neutral amino acid residues (other than Ser adjacent Cys); or $B^1$ and $B^2$ represent non-peptide spacer arms of a length equivalent to that determined by the length of d and c residues of amino acids c=0 to 4, d=0 to 4; and a=0 to 4 and b=0 to 4;

and wherein a positively charged amino acid residue is located on the peptide's N-terminal or C-terminal; the peptide or analogue thereof being capable of preventing the formation of or dissociating already formed 1 ga-$\alpha_1$AT complex.

* * * * *

SEQUENCE LISTING ( 1 ) GENERAL INFORMATION:

( i i i ) NUMBER OF SEQUENCES: 85

( 2 ) INFORMATION FOR SEQ ID NO: 1:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION:4
        ( D ) OTHER INFORMATION:/product="OTHER"
            / note= "AMIDATED"

( x i ) SEQUENCE DESCRIPTION: SEQ ID NO: 1:

His  Cys  Lys  Lys
      1

( 2 ) INFORMATION FOR SEQ ID NO: 2:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 2:

Phe  Asn  Ile  Gln  His  Cys  Lys  Lys  Leu  Ser  Ser
      1                      5                                  1 0

( 2 ) INFORMATION FOR SEQ ID NO: 3:

( i ) SEQUENCE CHARACTERISTICS:

(A) LENGTH: 4 amino acids
(B) TYPE: amino acid
(C) STRANDEDNESS: single
(D) TOPOLOGY: linear (i i) MOLECULE TYPE: peptide (i x) FEATURE:
(A) NAME/KEY: Modified-site
(B) LOCATION:4
(D) OTHER INFORMATION:/product="OTHER"
/ note= "AMIDATED"

(x i) SEQUENCE DESCRIPTION: SEQ ID NO: 3:

His Cys Lys Lys
1

(2) INFORMATION FOR SEQ ID NO: 4:

(i) SEQUENCE CHARACTERISTICS:
(A) LENGTH: 4 amino acids
(B) TYPE: amino acid
(C) STRANDEDNESS: single
(D) TOPOLOGY: linear (i i) MOLECULE TYPE: peptide (i x) FEATURE:
(A) NAME/KEY: Modified-site
(B) LOCATION:4
(D) OTHER INFORMATION:/product="OTHER"
/ note= "AMIDATED"

(x i) SEQUENCE DESCRIPTION: SEQ ID NO: 4:

His Cys Gly Lys
1

(2) INFORMATION FOR SEQ ID NO: 5:

(i) SEQUENCE CHARACTERISTICS:
(A) LENGTH: 4 amino acids
(B) TYPE: amino acid
(C) STRANDEDNESS: single
(D) TOPOLOGY: linear (i i) MOLECULE TYPE: peptide (i x) FEATURE:
(A) NAME/KEY: Modified-site
(B) LOCATION:4
(D) OTHER INFORMATION:/product="OTHER"
/ note= "AMIDATED"

(x i) SEQUENCE DESCRIPTION: SEQ ID NO: 5:

Lys Cys Gly Lys
1

(2) INFORMATION FOR SEQ ID NO: 6:

(i) SEQUENCE CHARACTERISTICS:
(A) LENGTH: 4 amino acids
(B) TYPE: amino acid
(C) STRANDEDNESS: single
(D) TOPOLOGY: linear (i i) MOLECULE TYPE: peptide (i x) FEATURE:
(A) NAME/KEY: Modified-site
(B) LOCATION:4
(D) OTHER INFORMATION:/product="OTHER"
/ note= "AMIDATED"

(x i) SEQUENCE DESCRIPTION: SEQ ID NO: 6:

Arg Cys Gly Lys
1

(2) INFORMATION FOR SEQ ID NO: 7:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION:5
        (D) OTHER INFORMATION:/product="OTHER"
            / note= "AMIDATED"

(xi) SEQUENCE DESCRIPTION: SEQ ID NO: 7:

His Cys Gly Gly Lys
1                5

(2) INFORMATION FOR SEQ ID NO: 8:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION:6
        (D) OTHER INFORMATION:/product="OTHER"
            / note= "AMIDATED"

(xi) SEQUENCE DESCRIPTION: SEQ ID NO: 8:

His Cys Gly Gly Gly Lys
1                5

(2) INFORMATION FOR SEQ ID NO: 9:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION:7
        (D) OTHER INFORMATION:/product="OTHER"
            / note= "AMIDATED"

(xi) SEQUENCE DESCRIPTION: SEQ ID NO: 9:

His Cys Gly Gly Gly Gly Lys
1                5

(2) INFORMATION FOR SEQ ID NO: 10:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide ( i x ) FEATURE:
  ( A ) NAME/KEY: Modified-site
  ( B ) LOCATION:4
  ( D ) OTHER INFORMATION:/product="OTHER"
    / note= "AMIDATED"

( x i ) SEQUENCE DESCRIPTION: SEQ ID NO: 10:

His Gly Cys Lys
1

( 2 ) INFORMATION FOR SEQ ID NO: 11:

( i ) SEQUENCE CHARACTERISTICS:
    ( A ) LENGTH: 5 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Modified-site
    ( B ) LOCATION:5
    ( D ) OTHER INFORMATION:/product="OTHER"
      / note= "AMIDATED"

( x i ) SEQUENCE DESCRIPTION: SEQ ID NO: 11:

His Gly Cys Gly Lys
1               5

( 2 ) INFORMATION FOR SEQ ID NO: 12:

( i ) SEQUENCE CHARACTERISTICS:
    ( A ) LENGTH: 6 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO: 12:

His Gly Cys Gly Gly Lys
1               5

( 2 ) INFORMATION FOR SEQ ID NO: 13:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Modified-site
    ( B ) LOCATION:7
    ( D ) OTHER INFORMATION:/product="OTHER"
      / note= "AMIDATED"

( x i ) SEQUENCE DESCRIPTION: SEQ ID NO: 13:

His Gly Cys Gly Gly Gly Lys
1               5

( 2 ) INFORMATION FOR SEQ ID NO: 14:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Modified-site
    ( B ) LOCATION:7
    ( D ) OTHER INFORMATION:/product="OTHER"
        / note= "AMIDATED"

( x i ) SEQUENCE DESCRIPTION: SEQ ID NO: 14:

His Gly Cys Gly Gly Gly Gly
1                  5

( 2 ) INFORMATION FOR SEQ ID NO: 15:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
    ( A ) NAME/KEY: Modified-site
    ( B ) LOCATION:5
    ( D ) OTHER INFORMATION:/product="OTHER"
        / note= "AMIDATED"

( x i ) SEQUENCE DESCRIPTION: SEQ ID NO: 15:

His Gly Gly Cys Lys
1             5

( 2 ) INFORMATION FOR SEQ ID NO: 16:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
    ( A ) NAME/KEY: Modified-site
    ( B ) LOCATION:6
    ( D ) OTHER INFORMATION:/product="OTHER"
        / note= "AMIDATED"

( x i ) SEQUENCE DESCRIPTION: SEQ ID NO: 16:

His Gly Gly Cys Gly Lys
1                5

( 2 ) INFORMATION FOR SEQ ID NO: 17:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
    ( A ) NAME/KEY: Modified-site
    ( B ) LOCATION:7
    ( D ) OTHER INFORMATION:/product="OTHER"
        / note= "AMIDATED"

( x i ) SEQUENCE DESCRIPTION: SEQ ID NO: 17:

His Gly Gly Cys Gly Gly Lys
1                  5

( 2 ) INFORMATION FOR SEQ ID NO: 18:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION:8
        ( D ) OTHER INFORMATION:/product="OTHER"
            / note= "AMIDATED"

( x i ) SEQUENCE DESCRIPTION: SEQ ID NO: 18:

His  Gly  Gly  Cys  Gly  Gly  Gly  Lys
    1                      5

( 2 ) INFORMATION FOR SEQ ID NO: 19:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION:9
        ( D ) OTHER INFORMATION:/product="OTHER"
            / note= "AMIDATED"

( x i ) SEQUENCE DESCRIPTION: SEQ ID NO: 19:

His  Gly  Gly  Cys  Gly  Gly  Gly  Gly  Lys
    1                      5

( 2 ) INFORMATION FOR SEQ ID NO: 20:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION:6
        ( D ) OTHER INFORMATION:/product="OTHER"
            / note= "AMIDATED"

( x i ) SEQUENCE DESCRIPTION: SEQ ID NO: 20:

His  Gly  Gly  Gly  Cys  Lys
    1                  5

( 2 ) INFORMATION FOR SEQ ID NO: 21:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION:7

(D) OTHER INFORMATION:/product="OTHER"
                /note= "AMIDATED"

(xi) SEQUENCE DESCRIPTION: SEQ ID NO: 21:

His   Gly   Gly   Gly   Cys   Gly   Lys
    1                       5

(2) INFORMATION FOR SEQ ID NO: 22:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site
            (B) LOCATION:8
            (D) OTHER INFORMATION:/product="OTHER"
                /note= "AMIDATED"

(xi) SEQUENCE DESCRIPTION: SEQ ID NO: 22:

His   Gly   Gly   Gly   Cys   Gly   Gly   Lys
    1                       5

(2) INFORMATION FOR SEQ ID NO: 23:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site
            (B) LOCATION:9
            (D) OTHER INFORMATION:/product="OTHER"
                /note= "AMIDATION"

(xi) SEQUENCE DESCRIPTION: SEQ ID NO: 23:

His   Gly   Gly   Gly   Cys   Gly   Gly   Gly   Lys
    1                       5

(2) INFORMATION FOR SEQ ID NO: 24:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site
            (B) LOCATION:10
            (D) OTHER INFORMATION:/product="OTHER"
                /note= "AMIDATED"

(xi) SEQUENCE DESCRIPTION: SEQ ID NO: 24:

His   Gly   Gly   Gly   Cys   Gly   Gly   Gly   Gly   Lys
    1                       5                             10

(2) INFORMATION FOR SEQ ID NO: 25:

(i) SEQUENCE CHARACTERISTICS:
            (A) LENGTH: 7 amino acids
            (B) TYPE: amino acid (C) STRANDEDNESS: single
(D) TOPOLOGY: linear (i i) MOLECULE TYPE: peptide (i x) FEATURE:
    (A) NAME/KEY: Modified-site
    (B) LOCATION:7
    (D) OTHER INFORMATION:/product="OTHER"
        / note= "AMIDATED"

(x i) SEQUENCE DESCRIPTION: SEQ ID NO: 25:

His Gly Gly Gly Gly Cys Lys
1               5

(2) INFORMATION FOR SEQ ID NO: 26:

(i) SEQUENCE CHARACTERISTICS:
    (A) LENGTH: 8 amino acids
    (B) TYPE: amino acid
    (C) STRANDEDNESS: single
    (D) TOPOLOGY: linear (i i) MOLECULE TYPE: peptide (i x) FEATURE:
    (A) NAME/KEY: Modified-site
    (B) LOCATION:8
    (D) OTHER INFORMATION:/product="OTHER"
        / note= "AMIDATED"

(x i) SEQUENCE DESCRIPTION: SEQ ID NO: 26:

His Gly Gly Gly Gly Cys Gly Lys
1               5

(2) INFORMATION FOR SEQ ID NO: 27:

(i) SEQUENCE CHARACTERISTICS:
    (A) LENGTH: 9 amino acids
    (B) TYPE: amino acid
    (C) STRANDEDNESS: single
    (D) TOPOLOGY: linear (i i) MOLECULE TYPE: peptide (i x) FEATURE:
    (A) NAME/KEY: Modified-site
    (B) LOCATION:9
    (D) OTHER INFORMATION:/product="OTHER"
        / note= "AMIDATED"

(x i) SEQUENCE DESCRIPTION: SEQ ID NO: 27:

His Gly Gly Gly Gly Cys Gly Gly Lys
1               5

(2) INFORMATION FOR SEQ ID NO: 28:

(i) SEQUENCE CHARACTERISTICS:
    (A) LENGTH: 10 amino acids
    (B) TYPE: amino acid
    (C) STRANDEDNESS: single
    (D) TOPOLOGY: linear (i i) MOLECULE TYPE: peptide (i x) FEATURE:
    (A) NAME/KEY: Modified-site
    (B) LOCATION:10
    (D) OTHER INFORMATION:/product="OTHER"
        / note= "AMIDATED"

(x i) SEQUENCE DESCRIPTION: SEQ ID NO: 28:

His Gly Gly Gly Gly Cys Gly Gly Gly Lys

```
            1               5                    1 0
```

( 2 ) INFORMATION FOR SEQ ID NO: 29:

( i ) SEQUENCE CHARACTERISTICS:
    ( A ) LENGTH: 11 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Modified-site
    ( B ) LOCATION:11
    ( D ) OTHER INFORMATION:/product="OTHER"
      / note= "AMIDATED"

( x i ) SEQUENCE DESCRIPTION: SEQ ID NO: 29:

```
His   Gly   Gly   Gly   Gly   Cys   Gly   Gly   Gly   Gly   Lys
1                       5                             1 0
```

( 2 ) INFORMATION FOR SEQ ID NO: 30:

( i ) SEQUENCE CHARACTERISTICS:
    ( A ) LENGTH: 5 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Modified-site
    ( B ) LOCATION:5
    ( D ) OTHER INFORMATION:/product="OTHER"
      / note= "AMIDATED"

( x i ) SEQUENCE DESCRIPTION: SEQ ID NO: 30:

```
His   Asp   Cys   Lys   Lys
1                       5
```

( 2 ) INFORMATION FOR SEQ ID NO: 31:

( i ) SEQUENCE CHARACTERISTICS:
    ( A ) LENGTH: 5 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Modified-site
    ( B ) LOCATION:5
    ( D ) OTHER INFORMATION:/product="OTHER"
      / note= "AMIDATED"

( x i ) SEQUENCE DESCRIPTION: SEQ ID NO: 31:

```
His   Tyr   Cys   Lys   Lys
1                       5
```

( 2 ) INFORMATION FOR SEQ ID NO: 32:

( i ) SEQUENCE CHARACTERISTICS:
    ( A ) LENGTH: 5 amino acids
    ( B ) TYPE: amino acid
    ( C ) STRANDEDNESS: single
    ( D ) TOPOLOGY: linear ( i i ) MOLECULE TYPE: peptide ( i x ) FEATURE:

(A) NAME/KEY: Modified-site
(B) LOCATION:5
(D) OTHER INFORMATION:/product="OTHER"
                        /note= "AMIDATED"

(xi) SEQUENCE DESCRIPTION: SEQ ID NO: 32:

His Pro Cys Lys Lys
1               5

(2) INFORMATION FOR SEQ ID NO: 33:

(i) SEQUENCE CHARACTERISTICS:
(A) LENGTH: 5 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION:5
(D) OTHER INFORMATION:/product="OTHER"
                        /note= "AMIDATED"

(xi) SEQUENCE DESCRIPTION: SEQ ID NO: 33:

His Glu Cys Lys Lys
1               5

(2) INFORMATION FOR SEQ ID NO: 34:

(i) SEQUENCE CHARACTERISTICS:
(A) LENGTH: 5 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION:5
(D) OTHER INFORMATION:/product="OTHER"
                        /note= "AMIDATED"

(xi) SEQUENCE DESCRIPTION: SEQ ID NO: 34:

His Phe Cys Lys Lys
1               5

(2) INFORMATION FOR SEQ ID NO: 35:

(i) SEQUENCE CHARACTERISTICS:
(A) LENGTH: 4 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION:4
(D) OTHER INFORMATION:/product="OTHER"
                        /note= "AMIDATED"

(xi) SEQUENCE DESCRIPTION: SEQ ID NO: 35:

Cys His Gly Lys
1

(2) INFORMATION FOR SEQ ID NO: 36:

(i) SEQUENCE CHARACTERISTICS:

( A ) LENGTH: 5 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Modified-site
( B ) LOCATION:5
( D ) OTHER INFORMATION:/product="OTHER"
/ note= "AMIDATED"

( x i ) SEQUENCE DESCRIPTION: SEQ ID NO: 36:

Cys His Gly Gly Lys
1               5

( 2 ) INFORMATION FOR SEQ ID NO: 37:

( i ) SEQUENCE CHARACTERISTICS:
( A ) LENGTH: 6 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Modified-site
( B ) LOCATION:6
( D ) OTHER INFORMATION:/product="OTHER"
/ note= "AMIDATED"

( x i ) SEQUENCE DESCRIPTION: SEQ ID NO: 37:

Cys His Gly Gly Gly Lys
1               5

( 2 ) INFORMATION FOR SEQ ID NO: 38:

( i ) SEQUENCE CHARACTERISTICS:
( A ) LENGTH: 7 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Modified-site
( B ) LOCATION:7
( D ) OTHER INFORMATION:/product="OTHER"
/ note= "AMIDATED"

( x i ) SEQUENCE DESCRIPTION: SEQ ID NO: 38:

Cys His Gly Gly Gly Gly Lys
1               5

( 2 ) INFORMATION FOR SEQ ID NO: 39:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Modified-site
( B ) LOCATION:4
( D ) OTHER INFORMATION:/product="OTHER"
/ note= "AMIDATED"

( x i ) SEQUENCE DESCRIPTION: SEQ ID NO: 39:

Cys  Gly  His  Lys
1

(2) INFORMATION FOR SEQ ID NO: 40:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION:5
        (D) OTHER INFORMATION:/product="OTHER"
            / note= "AMIDATED"

(xi) SEQUENCE DESCRIPTION: SEQ ID NO: 40:

Cys  Gly  Gly  His  Lys
1                    5

(2) INFORMATION FOR SEQ ID NO: 41:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION:6
        (D) OTHER INFORMATION:/product="OTHER"
            / note= "AMIDATED"

(xi) SEQUENCE DESCRIPTION: SEQ ID NO: 41:

Cys  Gly  Gly  Gly  His  Lys
1                    5

(2) INFORMATION FOR SEQ ID NO: 42:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION:7
        (D) OTHER INFORMATION:/product="OTHER"
            / note= "AMIDATED"

(xi) SEQUENCE DESCRIPTION: SEQ ID NO: 42:

Cys  Gly  Gly  Gly  Gly  His  Lys
1                    5

(2) INFORMATION FOR SEQ ID NO: 43:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide ( i x ) FEATURE:
   ( A ) NAME/KEY: Modified-site
   ( B ) LOCATION:4
   ( D ) OTHER INFORMATION:/product="OTHER"
    / note= "AMIDATED"

( x i ) SEQUENCE DESCRIPTION: SEQ ID NO: 43:

His Lys Gly Cys
1

( 2 ) INFORMATION FOR SEQ ID NO: 44:

( i ) SEQUENCE CHARACTERISTICS:
   ( A ) LENGTH: 5 amino acids
   ( B ) TYPE: amino acid
   ( C ) STRANDEDNESS: single
   ( D ) TOPOLOGY: linear ( i i ) MOLECULE TYPE: peptide ( i x ) FEATURE:
   ( A ) NAME/KEY: Modified-site
   ( B ) LOCATION:5
   ( D ) OTHER INFORMATION:/product="OTHER"
    / note= "AMIDATED"

( x i ) SEQUENCE DESCRIPTION: SEQ ID NO: 44:

His Lys Gly Gly Cys
1      5

( 2 ) INFORMATION FOR SEQ ID NO: 45:

( i ) SEQUENCE CHARACTERISTICS:
   ( A ) LENGTH: 6 amino acids
   ( B ) TYPE: amino acid
   ( C ) STRANDEDNESS: single
   ( D ) TOPOLOGY: linear ( i i ) MOLECULE TYPE: peptide ( i x ) FEATURE:
   ( A ) NAME/KEY: Modified-site
   ( B ) LOCATION:6
   ( D ) OTHER INFORMATION:/product="OTHER"
    / note= "AMIDATED"

( x i ) SEQUENCE DESCRIPTION: SEQ ID NO: 45:

His Lys Gly Gly Gly Cys
1      5

( 2 ) INFORMATION FOR SEQ ID NO: 46:

( i ) SEQUENCE CHARACTERISTICS:
   ( A ) LENGTH: 7 amino acids
   ( B ) TYPE: amino acid
   ( C ) STRANDEDNESS: single
   ( D ) TOPOLOGY: linear ( i i ) MOLECULE TYPE: peptide ( i x ) FEATURE:
   ( A ) NAME/KEY: Modified-site
   ( B ) LOCATION:7
   ( D ) OTHER INFORMATION:/product="OTHER"
    / note= "AMIDATED"

( x i ) SEQUENCE DESCRIPTION: SEQ ID NO: 46:

His Lys Gly Gly Gly Gly Cys
1      5

( 2 ) INFORMATION FOR SEQ ID NO: 47:

( i ) SEQUENCE CHARACTERISTICS:
    ( A ) LENGTH: 4 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Modified-site
    ( B ) LOCATION:4
    ( D ) OTHER INFORMATION:/product="OTHER"
        / note= "AMIDATED"

( x i ) SEQUENCE DESCRIPTION: SEQ ID NO: 47:

His Gly Lys Cys
1

( 2 ) INFORMATION FOR SEQ ID NO: 48:

( i ) SEQUENCE CHARACTERISTICS:
    ( A ) LENGTH: 5 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Modified-site
    ( B ) LOCATION:5
    ( D ) OTHER INFORMATION:/product="OTHER"
        / note= "AMIDATED"

( x i ) SEQUENCE DESCRIPTION: SEQ ID NO: 48:

His Gly Gly Lys Cys
1                        5

( 2 ) INFORMATION FOR SEQ ID NO: 49:

( i ) SEQUENCE CHARACTERISTICS:
    ( A ) LENGTH: 6 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Modified-site
    ( B ) LOCATION:6
    ( D ) OTHER INFORMATION:/product="OTHER"
        / note= "AMIDATED"

( x i ) SEQUENCE DESCRIPTION: SEQ ID NO: 49:

His Gly Gly Gly Lys Cys
1                        5

( 2 ) INFORMATION FOR SEQ ID NO: 50:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Modified-site
    ( B ) LOCATION:7
    ( D ) OTHER INFORMATION:/product="OTHER"
        / note= "AMIDATED"

( x i ) SEQUENCE DESCRIPTION: SEQ ID NO: 50:

His Gly Gly Gly Gly Lys Cys
1               5

( 2 ) INFORMATION FOR SEQ ID NO: 51:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION:5
        ( D ) OTHER INFORMATION:/product="OTHER"
            / note= "AMIDATED"

( x i ) SEQUENCE DESCRIPTION: SEQ ID NO: 51:

His Gly Lys Gly Cys
1           5

( 2 ) INFORMATION FOR SEQ ID NO: 52:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION:5
        ( D ) OTHER INFORMATION:/product="OTHER"
            / note= "AMIDATED"

( x i ) SEQUENCE DESCRIPTION: SEQ ID NO: 52:

Asp His Cys Lys Lys
1           5

( 2 ) INFORMATION FOR SEQ ID NO: 53:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION:5
        ( D ) OTHER INFORMATION:/product="OTHER"
            / note= "AMIDATED"

( x i ) SEQUENCE DESCRIPTION: SEQ ID NO: 53:

Glu His Cys Lys Lys
1           5

( 2 ) INFORMATION FOR SEQ ID NO: 54:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
    ( A ) NAME/KEY: Modified-site
    ( B ) LOCATION:6
    ( D ) OTHER INFORMATION:/product="OTHER"
        / note= "AMIDATED"

( x i ) SEQUENCE DESCRIPTION: SEQ ID NO: 54:

```
Asp  Gly  His  Cys  Lys  Lys
1                    5
```

( 2 ) INFORMATION FOR SEQ ID NO: 55:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
    ( A ) NAME/KEY: Modified-site
    ( B ) LOCATION:6
    ( D ) OTHER INFORMATION:/product="OTHER"
        / note= "AMIDATED"

( x i ) SEQUENCE DESCRIPTION: SEQ ID NO: 55:

```
His  Lys  Gly  Gly  Gly  Cys
1                    5
```

( 2 ) INFORMATION FOR SEQ ID NO: 56:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
    ( A ) NAME/KEY: Modified-site
    ( B ) LOCATION:6
    ( D ) OTHER INFORMATION:/product="OTHER"
        / note= "AMIDATED"

( x i ) SEQUENCE DESCRIPTION: SEQ ID NO: 56:

```
Glu  Gly  His  Cys  Lys  Lys
1                    5
```

( 2 ) INFORMATION FOR SEQ ID NO: 57:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
    ( A ) NAME/KEY: Modified-site
    ( B ) LOCATION:7
    ( D ) OTHER INFORMATION:/product="OTHER"
        / note= "AMIDATED"

( x i ) SEQUENCE DESCRIPTION: SEQ ID NO: 57:

```
Asp  Gly  Gly  His  Cys  Lys  Lys
1                    5
```

( 2 ) INFORMATION FOR SEQ ID NO: 58:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION:8
        ( D ) OTHER INFORMATION:/product="OTHER"
            / note= "AMIDATED"

( x i ) SEQUENCE DESCRIPTION: SEQ ID NO: 58:

Asp Gly Gly Gly His Cys Lys Lys
1               5

( 2 ) INFORMATION FOR SEQ ID NO: 59:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION:9
        ( D ) OTHER INFORMATION:/product="OTHER"
            / note= "AMIDATED"

( x i ) SEQUENCE DESCRIPTION: SEQ ID NO: 59:

Asp Gly Gly Gly Gly His Cys Lys Lys
1               5

( 2 ) INFORMATION FOR SEQ ID NO: 60:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION:10
        ( D ) OTHER INFORMATION:/product="OTHER"
            / note= "AMIDATED"

( x i ) SEQUENCE DESCRIPTION: SEQ ID NO: 60:

Asp Gly Gly Gly Gly Gly His Cys Lys Lys
1               5                   1 0

( 2 ) INFORMATION FOR SEQ ID NO: 61:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION:5

( D ) OTHER INFORMATION:/product="OTHER"
/ note= "AMIDATED"

( x i ) SEQUENCE DESCRIPTION: SEQ ID NO: 61:

Gln His Cys Lys Lys
1               5

( 2 ) INFORMATION FOR SEQ ID NO: 62:

( i ) SEQUENCE CHARACTERISTICS:
( A ) LENGTH: 6 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Modified-site
( B ) LOCATION:6
( D ) OTHER INFORMATION:/product="OTHER"
/ note= "AMIDATED"

( x i ) SEQUENCE DESCRIPTION: SEQ ID NO: 62:

Ile Gln His Cys Lys Lys
1               5

( 2 ) INFORMATION FOR SEQ ID NO: 63:

( i ) SEQUENCE CHARACTERISTICS:
( A ) LENGTH: 7 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Modified-site
( B ) LOCATION:7
( D ) OTHER INFORMATION:/product="OTHER"
/ note= "AMIDATED"

( x i ) SEQUENCE DESCRIPTION: SEQ ID NO: 63:

Asn Ile Gln His Cys Lys Lys
1               5

( 2 ) INFORMATION FOR SEQ ID NO: 64:

( i ) SEQUENCE CHARACTERISTICS:
( A ) LENGTH: 8 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Modified-site
( B ) LOCATION:8
( D ) OTHER INFORMATION:/product="OTHER"
/ note= "AMIDATED"

( x i ) SEQUENCE DESCRIPTION: SEQ ID NO: 64:

Phe Asn Ile Gln His Cys Lys Lys
1               5

( 2 ) INFORMATION FOR SEQ ID NO: 65:

( i ) SEQUENCE CHARACTERISTICS:
( A ) LENGTH: 9 amino acids
( B ) TYPE: amino acid ( C ) STRANDEDNESS: single
( D ) TOPOLOGY: linear ( i i ) MOLECULE TYPE: peptide ( i x ) FEATURE:
( A ) NAME/KEY: Modified-site
( B ) LOCATION:9
( D ) OTHER INFORMATION:/product="OTHER"
/ note= "AMIDATED"

( x i ) SEQUENCE DESCRIPTION: SEQ ID NO: 65:

Met Phe Asn Ile Gln His Cys Lys Lys
1               5

( 2 ) INFORMATION FOR SEQ ID NO: 66:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Modified-site
( B ) LOCATION:5
( D ) OTHER INFORMATION:/product="OTHER"
/ note= "AMIDATED"

( x i ) SEQUENCE DESCRIPTION: SEQ ID NO: 66:

His Cys Lys Lys Asp
1               5

( 2 ) INFORMATION FOR SEQ ID NO: 67:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Modified-site
( B ) LOCATION:5
( D ) OTHER INFORMATION:/product="OTHER"
/ note= "AMIDATED"

( x i ) SEQUENCE DESCRIPTION: SEQ ID NO: 67:

His Cys Lys Lys Glu
1               5

( 2 ) INFORMATION FOR SEQ ID NO: 68:

( i ) SEQUENCE CHARACTERISTICS:
( A ) LENGTH: 6 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Modified-site
( B ) LOCATION:6
( D ) OTHER INFORMATION:/product="OTHER"
/ note= "AMIDATED"

( x i ) SEQUENCE DESCRIPTION: SEQ ID NO: 68:

His Cys Lys Lys Gly Asp

```
        1               5
```

( 2 ) INFORMATION FOR SEQ ID NO: 69:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION:6
        ( D ) OTHER INFORMATION:/product="OTHER"
            / note= "AMIDATED"

( x i ) SEQUENCE DESCRIPTION: SEQ ID NO: 69:

```
His   Cys   Lys   Lys   Gly   Glu
1                         5
```

( 2 ) INFORMATION FOR SEQ ID NO: 70:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION:7
        ( D ) OTHER INFORMATION:/product="OTHER"
            / note= "AMIDATED"

( x i ) SEQUENCE DESCRIPTION: SEQ ID NO: 70:

```
His   Cys   Lys   Lys   Gly   Gly   Asp
1                         5
```

( 2 ) INFORMATION FOR SEQ ID NO: 71:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION:7
        ( D ) OTHER INFORMATION:/product="OTHER"
            / note= "AMIDATED"

( x i ) SEQUENCE DESCRIPTION: SEQ ID NO: 71:

```
His   Cys   Lys   Lys   Gly   Gly   Glu
1                         5
```

( 2 ) INFORMATION FOR SEQ ID NO: 72:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i x ) FEATURE:

( A ) NAME/KEY: Modified-site
( B ) LOCATION:8
( D ) OTHER INFORMATION:/product="OTHER"
         / note= "AMIDATED"

( x i ) SEQUENCE DESCRIPTION: SEQ ID NO: 72:

His  Cys  Lys  Lys  Gly  Gly  Gly  Asp
1                   5

( 2 ) INFORMATION FOR SEQ ID NO: 73:

( i ) SEQUENCE CHARACTERISTICS:
      ( A ) LENGTH: 8 amino acids
      ( B ) TYPE: amino acid
      ( C ) STRANDEDNESS: single
      ( D ) TOPOLOGY: linear ( i i ) MOLECULE TYPE: peptide ( i x ) FEATURE:
      ( A ) NAME/KEY: Modified-site
      ( B ) LOCATION:8
      ( D ) OTHER INFORMATION:/product="OTHER"
         / note= "AMIDATED"

( x i ) SEQUENCE DESCRIPTION: SEQ ID NO: 73:

His  Cys  Lys  Lys  Gly  Gly  Gly  Glu
1                   5

( 2 ) INFORMATION FOR SEQ ID NO: 74:

( i ) SEQUENCE CHARACTERISTICS:
      ( A ) LENGTH: 7 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO: 74:

Glu  Val  Asp  Gly  Thr  Cys  Tyr
1                   5

( 2 ) INFORMATION FOR SEQ ID NO: 75:

( i ) SEQUENCE CHARACTERISTICS:
      ( A ) LENGTH: 6 amino acids
      ( B ) TYPE: amino acid
      ( C ) STRANDEDNESS: single
      ( D ) TOPOLOGY: linear ( i i ) MOLECULE TYPE: peptide ( i x ) FEATURE:
      ( A ) NAME/KEY: Modified-site
      ( B ) LOCATION:6
      ( D ) OTHER INFORMATION:/product="OTHER"
         / note= "AMIDATED"

( x i ) SEQUENCE DESCRIPTION: SEQ ID NO: 75:

Val  Asp  Gly  Thr  Cys  Tyr
1                   5

( 2 ) INFORMATION FOR SEQ ID NO: 76:

( i ) SEQUENCE CHARACTERISTICS:
      ( A ) LENGTH: 5 amino acids
      ( B ) TYPE: amino acid
      ( C ) STRANDEDNESS: single
      ( D ) TOPOLOGY: linear ( i i ) MOLECULE TYPE: peptide (x i) SEQUENCE DESCRIPTION: SEQ ID NO: 76:

Asp Gly Thr Cys Tyr
1               5

(2) INFORMATION FOR SEQ ID NO: 77:

(i) SEQUENCE CHARACTERISTICS:
      (A) LENGTH: 4 amino acids
      (B) TYPE: amino acid
      (C) STRANDEDNESS: single
      (D) TOPOLOGY: linear (i i) MOLECULE TYPE: peptide (x i) SEQUENCE DESCRIPTION: SEQ ID NO: 77:

Gly Thr Cys Tyr
1

(2) INFORMATION FOR SEQ ID NO: 78:

(i) SEQUENCE CHARACTERISTICS:
      (A) LENGTH: 4 amino acids
      (B) TYPE: amino acid
      (C) STRANDEDNESS: single
      (D) TOPOLOGY: linear (i i) MOLECULE TYPE: peptide (x i) SEQUENCE DESCRIPTION: SEQ ID NO: 78:

His Cys Lys Lys
1

(2) INFORMATION FOR SEQ ID NO: 79:

(i) SEQUENCE CHARACTERISTICS:
      (A) LENGTH: 10 amino acids
      (B) TYPE: amino acid
      (C) STRANDEDNESS: single
      (D) TOPOLOGY: linear (i i) MOLECULE TYPE: peptide (x i) SEQUENCE DESCRIPTION: SEQ ID NO: 79:

Lys Thr Lys Gly Ser Gly Phe Phe Val Phe
1               5                   10

(2) INFORMATION FOR SEQ ID NO: 80:

(i) SEQUENCE CHARACTERISTICS:
      (A) LENGTH: 13 amino acids
      (B) TYPE: amino acid
      (C) STRANDEDNESS: single
      (D) TOPOLOGY: linear (i i) MOLECULE TYPE: peptide (x i) SEQUENCE DESCRIPTION: SEQ ID NO: 80:

Val Ser Val Val Met Ala Glu Val Asp Gly Thr Cys Tyr
1               5                   10

(2) INFORMATION FOR SEQ ID NO: 81:

(i) SEQUENCE CHARACTERISTICS:
      (A) LENGTH: 12 amino acids
      (B) TYPE: amino acid
      (C) STRANDEDNESS: single
      (D) TOPOLOGY: linear (i i) MOLECULE TYPE: peptide ( x i ) SEQUENCE DESCRIPTION: SEQ ID NO: 81:

Ile Val Leu Val Asp Asn Lys Cys Lys Cys Ala Arg
1               5                   10

( 2 ) INFORMATION FOR SEQ ID NO: 82:

( i ) SEQUENCE CHARACTERISTICS:
      ( A ) LENGTH: 13 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO: 82:

Gly Met Phe Asn Ile Gln His Cys Lys Lys Leu Ser Ser
1               5                   10

( 2 ) INFORMATION FOR SEQ ID NO: 83:

( i ) SEQUENCE CHARACTERISTICS:
      ( A ) LENGTH: 5 amino acids
      ( B ) TYPE: amino acid
      ( C ) STRANDEDNESS: single
      ( D ) TOPOLOGY: linear ( i i ) MOLECULE TYPE: peptide ( i x ) FEATURE:
      ( A ) NAME/KEY: Modified-site
      ( B ) LOCATION:5
      ( D ) OTHER INFORMATION:/product="OTHER"
          / note= "AMIDATED"

( x i ) SEQUENCE DESCRIPTION: SEQ ID NO: 83:

His Cys Cys Gly Lys
1               5

( 2 ) INFORMATION FOR SEQ ID NO: 84:

( i ) SEQUENCE CHARACTERISTICS:
      ( A ) LENGTH: 5 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO: 84:

Lys Ala Ala Gly Ser
1               5

( 2 ) INFORMATION FOR SEQ ID NO: 85:

( i ) SEQUENCE CHARACTERISTICS:
      ( A ) LENGTH: 5 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO: 85:

Asp His Cys Lys Lys
1               5